US009555268B2

(12) United States Patent
Clark

(10) Patent No.: US 9,555,268 B2
(45) Date of Patent: Jan. 31, 2017

(54) SPHERICAL ULTRASONIC HIFU TRANSDUCER WITH MODULAR CAVITATION SENSE ELEMENT

(75) Inventor: Dennis Dean Clark, Lewistown, PA (US)

(73) Assignee: Koninklijke Philips N.V., Eindhoven (NL)

( * ) Notice: Subject to any disclaimer, the term of this patent is extended or adjusted under 35 U.S.C. 154(b) by 137 days.

(21) Appl. No.: 14/113,670

(22) PCT Filed: May 8, 2012

(86) PCT No.: PCT/IB2012/052278
§ 371 (c)(1),
(2), (4) Date: Oct. 24, 2013

(87) PCT Pub. No.: WO2012/156863
PCT Pub. Date: Nov. 22, 2012

(65) Prior Publication Data
US 2014/0058297 A1    Feb. 27, 2014

Related U.S. Application Data

(60) Provisional application No. 61/487,308, filed on May 18, 2011.

(51) Int. Cl.
| A61B 8/00 | (2006.01) |
| A61N 7/02 | (2006.01) |
| A61B 17/00 | (2006.01) |
| A61B 17/22 | (2006.01) |
| A61N 7/00 | (2006.01) |

(52) U.S. Cl.
CPC ....... *A61N 7/02* (2013.01); *A61B 2017/00106* (2013.01); *A61B 2017/22008* (2013.01); *A61N 2007/0065* (2013.01)

(58) Field of Classification Search
USPC ............................................................ 601/3
See application file for complete search history.

(56) References Cited

U.S. PATENT DOCUMENTS

| 4,633,122 A | 12/1986 | Radice |
| 5,119,801 A | 6/1992 | Eizenhoefer et al. |
| 5,493,541 A | 2/1996 | Snyder |
| 5,523,058 A | 6/1996 | Umemura |
| 5,743,862 A | 4/1998 | Izumi |
| 5,827,204 A | 10/1998 | Grandia et al. |
| 6,374,132 B1 | 4/2002 | Acker et al. |

(Continued)

FOREIGN PATENT DOCUMENTS

| JP | 03133300 | 6/1991 |
| WO | 2011055316 A1 | 5/2011 |
| WO | 2012042423 A1 | 9/2011 |

*Primary Examiner* — Patricia Park

(57) ABSTRACT

An ultrasonic HIFU transducer (120) has a threaded opening into which a modular cavitation sensor (90) is removably located. The modular cavitation sensor includes a modular housing (92) containing a piezoelectric transducer for sensing acoustic signals indicative of cavitation. The modular cavitation sensor has electrodes (96,98) which engage spring contacts (112,114) in the threaded opening when the modular housing is screwed into the threaded opening. A damaged sensor can be unscrewed and replaced simply without connectors or soldering.

20 Claims, 7 Drawing Sheets

(56) References Cited

U.S. PATENT DOCUMENTS

| | | | |
|---|---|---|---|
| 6,820,313 B2 | 11/2004 | Gauchet | |
| 7,602,672 B2 | 10/2009 | Lai et al. | |
| 8,568,322 B2 | 10/2013 | Lacoste | |
| 2003/0018267 A1 | 1/2003 | Erikson et al. | |
| 2004/0050163 A1* | 3/2004 | Komninos | 73/587 |
| 2004/0102888 A1* | 5/2004 | Burgdorf et al. | 701/70 |
| 2007/0282204 A1 | 12/2007 | Yamashita et al. | |
| 2008/0249419 A1* | 10/2008 | Sekins | A61B 8/08 600/463 |
| 2009/0230822 A1* | 9/2009 | Kushculey et al. | 310/366 |
| 2009/0287083 A1 | 11/2009 | Kushculey et al. | |
| 2010/0056924 A1 | 3/2010 | Powers | |
| 2010/0331686 A1 | 12/2010 | Hossack et al. | |
| 2011/0105952 A1* | 5/2011 | Bernstein et al. | 600/573 |

* cited by examiner

SPHERICAL ULTRASONIC HIFU TRANSDUCER WITH MODULAR CAVITATION SENSE ELEMENT

This application is the U.S. National Phase application under 35 U.S.C. §371 of International Application No. PCT/2012/052278, filed on May 8, 2012, which claims the benefit of U.S. Provisional application 61/487,308, filed on May 18, 2011. These applications are hereby incorporated by reference herein.

This invention relates to medical diagnostic ultrasound systems and, in particular, to ultrasonic transducers which are used for controlled heating of body tissues by high intensity focused ultrasound, known as HIFU.

Ultrasonically delivered elevated temperature treatments are used for a variety of therapeutic purposes In HIFU treatment, ultrasonic energy is focused to a small spot within the body so as to heat the tissues to a temperature sufficient to create a desired therapeutic effect. The technique is similar to lithotripsy, where focused energy is high enough to break up kidney stones, but with considerably less energy that is delivered over an extended time rather than a sudden pulse. The HIFU technique can be used to selectively destroy unwanted tissue within the body. For example, tumors or other pathological tissues can be destroyed by applying focused ultrasonic energy so as to heat the cells to a temperature sufficient to kill the tissue, generally about 60 to about 80 degrees C., without destroying adjacent normal tissues. Other elevated-temperature treatments include selectively heating tissues so as to selectively activate a drug or to promote some other physiological change in a selected portion of the subject's body.

HIFU transducers are often formed as spherical or parabolic dishes with a radius of curvature that gives the transducer a geometric focal point. See, for example, the HIFU transducer described in international patent application IB2010/054985, filed Nov. 3, 2010. The transducer described in this application is formed of a small number of composite ceramic piezoelectric tiles. The tiles are curved in two dimensions so that they will fit together to form the desired spherical transmitting surface of a desired geometric focus. Each tile can be individually fabricated and tested before assembly, assuring that the complete transducer will be fully function as specified after assembly. Such composite ceramic piezoelectric tiles can exhibit an energy conversion efficiency of 80-85% during transmission.

When destroying tissue cells by thermal effects, it is generally desirable to avoid the development of higher ultrasonic energy levels that will produce more deleterious effects such as cavitation. Consequently HIFU transducers often include a cavitation sensor which is used to monitor for evidence of cavitation. Stable and inertial cavitation can be detected by the appearance of certain noise and harmonic signal levels as described in U.S. provisional patent application No. 61/392,067 entitled "MONITORING AND CONTROL OF MICROBUBBLE CAVITATION IN THERAPEUTIC ULTRASOUND" (Vignon et al.) See also U.S. Pat. No. 5,827,204 (Grandia et al.) which uses a hydrophone to detect acoustic evidence of cavitation. The cavitation sensor is generally bonded at the center of the HIFU transducer. However, when the HIFU transducer is shaped spherically or parabolically for focusing, it has been found that the center of the dish shape can receive energy and heat reflected back from the interface of the transducer's fluid bath and acoustic window. This heat and energy can focus at the center of the HIFU transducer and damage the cavitation sensor. A damaged cavitation sensor, whether from reflected energy or damage during the manufacturing process, can render the entire transducer unacceptable, even if the HIFU elements themselves are still fully functional. Hence it is desirable to be able to repair the transducer and its cavitation sensor to obviate the need to scrap an otherwise functional HIFU transducer.

In accordance with the principles of the present invention, a spherical HIFU transducer is described with a modularly mounted cavitation sensor. In the described implementation a mount for the cavitation sensor is threaded into an opening at the center of the HIFU transducer and sealed against fluid egress with an O ring. Signal connection are made to contact areas of the cavitation sensor by spring contacts, so the cavitation sensor can be replaced with a new sensor without the need for soldering. Should the cavitation sensor become damaged, the sensor mount can be unscrewed and a new sensor inserted in place of the damaged sensor and threaded into the same location.

Figure 9:
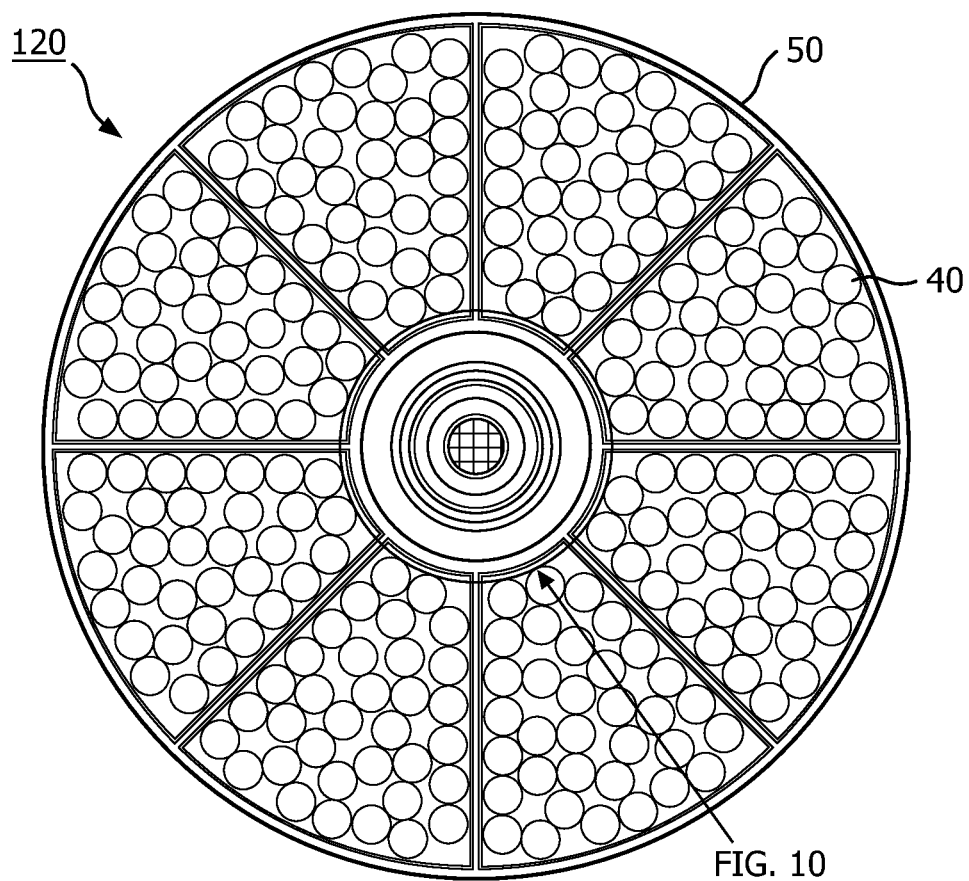
Figure 10:
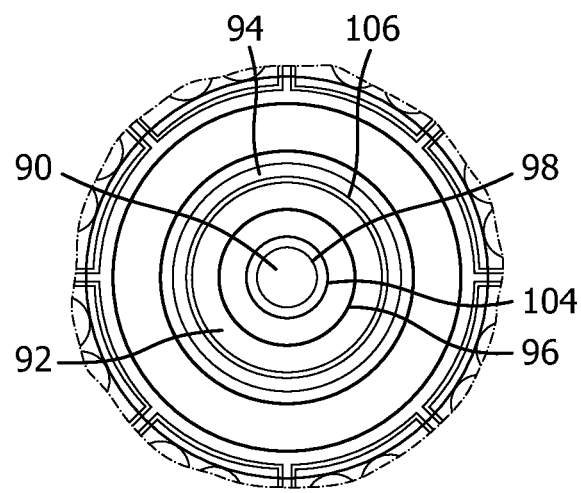

FIGS. 9 and 10 illustrated a modular cavitation sensor mounted in a HIFU transducer in accordance with the principles of the present invention.

Figure 12:
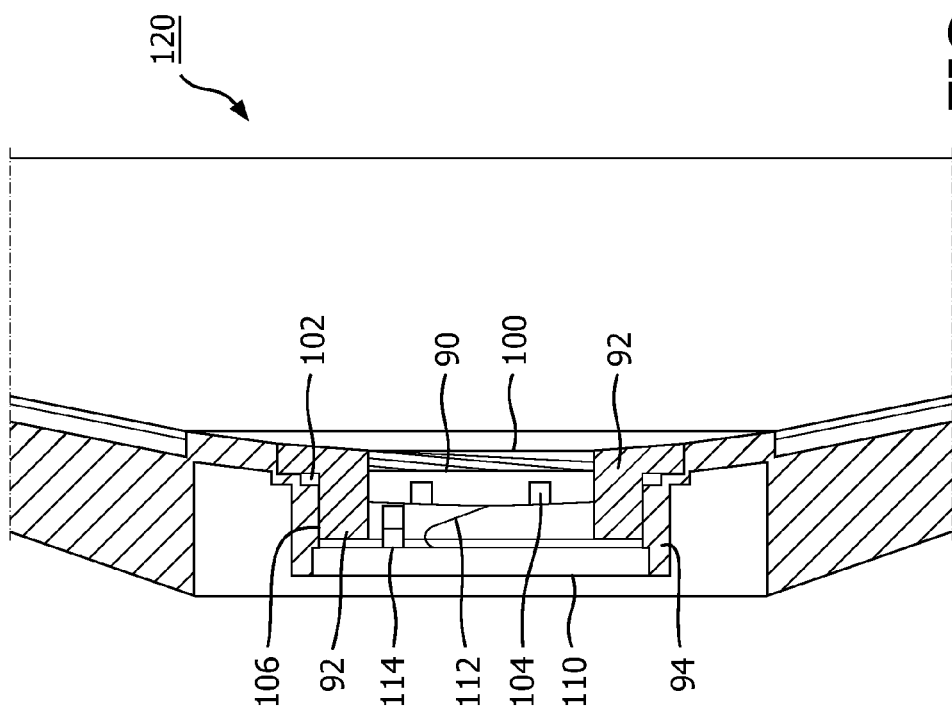
Figure 11:
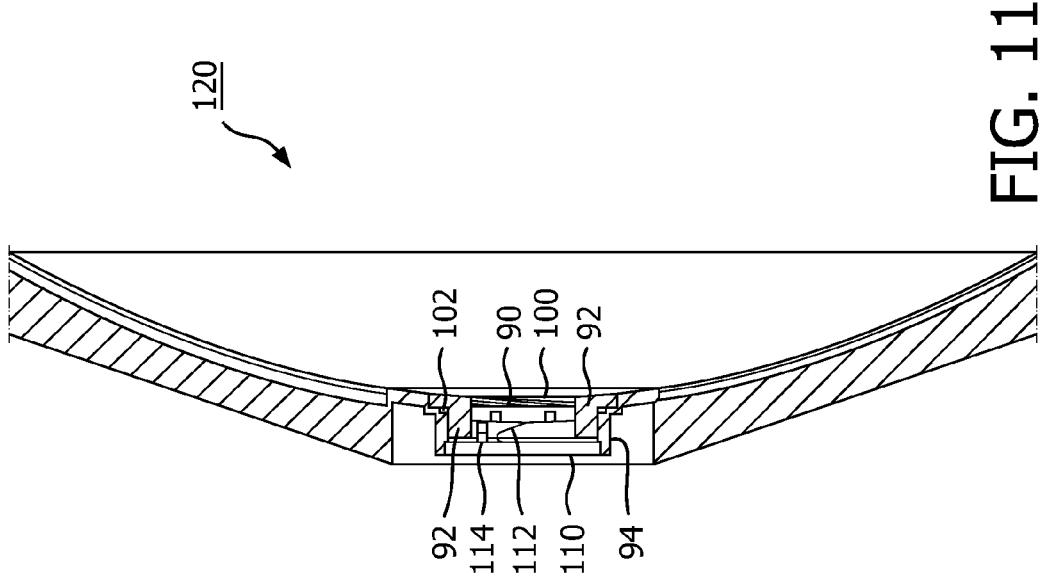

FIGS. 11 and 12 are cross-sectional views of a HIFU transducer with a modular cavitation sensor.

Figure 1:
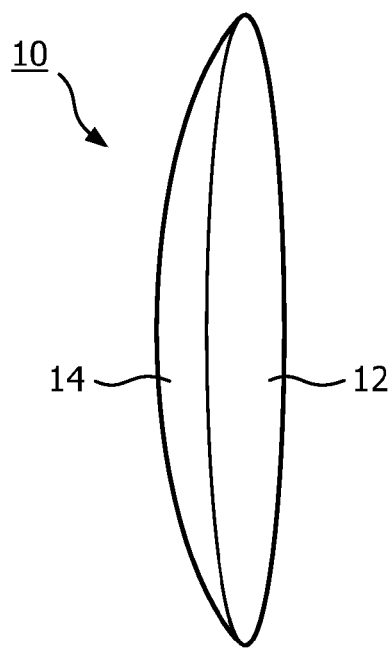
FIG. 1 illustrates in perspective a spherical transducer matching layer separately formed for a HIFU transducer of the present invention.

Construction of a HIFU transducer of the present invention may begin with fabrication of a spherical or dish-shaped matching layer. The matching layer(s) of a transducer provide at least a partial matching of the acoustic properties of the piezoelectric transducer to the acoustic properties of the patient's body or the medium between the transducer and the patient. The properties matched may include acoustic impedance, velocity of sound, and material density. In the conventional construction of an ultrasound transducer the matching layer is generally formed on the transducer stack and is formed over the reference electrodes on the emitting surface of the piezoelectric material. For the HIFU transducer described in this disclosure a spherical matching layer is formed by itself, separate from the rest of the transducer. There are several ways to form the spherical matching layer, including casting, molding, thermoforming, or machining. The spherical matching layer of the HIFU transducer described herein is made of a loaded epoxy which is loaded with particles which provide the matching layer with its desired acoustic properties as is known in the art. Preferably the particles are non-magnetic. In casting or molding the spherical matching layer, the loaded epoxy is poured into a concave fixture of the desired spherical shape. A convex fixture is closed over the concave fixture, forcing the liquid epoxy to fill the spherical space between the two fixtures. The epoxy is cured and removed from the fixtures, then peripherally machined to its final form. In a thermoform process a planar sheet of the desired thickness is formed of the loaded epoxy, then partially cured. The sheet is then placed over a heated convex or concave fixture of the desired curvature which warms the sheet so that it becomes pliant and conforms to the curvature of the fixture. When the sheet has attained its desired spherical shape it is cured and finished. In a machining process a disk of loaded epoxy is cast or molded and cured. The disk is then machined on one side to form a convex surface. The disk is then put on a concave fixture and the other side of the disk is machined to form the concave side of the spherical matching layer. In a constructed embodiment the finished spherical matching layer from any of these processes is 0.5 mm thick, has a diameter of 140 mm, and a spherical radius of 140 mm, the size and shape of the finished HIFU transducer. FIG. 1 illustrates such a spherical matching layer 10. The concave surface 12 is the emitting surface of the finished transducer which faces the patient and the convex surface 14 is sputtered to produce a redundant signal return electrode, then covered with composite piezoelectric tiles. The rigid matching layer thus provides a form of the desired curvature for assembly of the piezoelectric tile layer. Since the matching layer 10 in front of the tiles is a continuously formed surface, it provides the desired electrical and environmental isolation of the rest of the HIFU transducer from the patient and the external surroundings in front of the HIFU transducer.

Figure 2A:
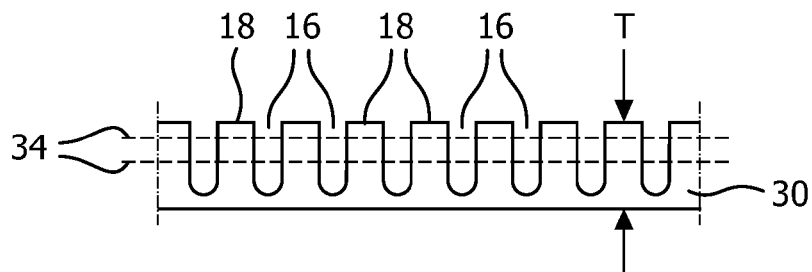
FIG. 2a illustrates an end view of a sheet of ceramic piezoelectric material which has been diced to form a composite transducer array for a HIFU transducer of the present invention.
Figure 2B:
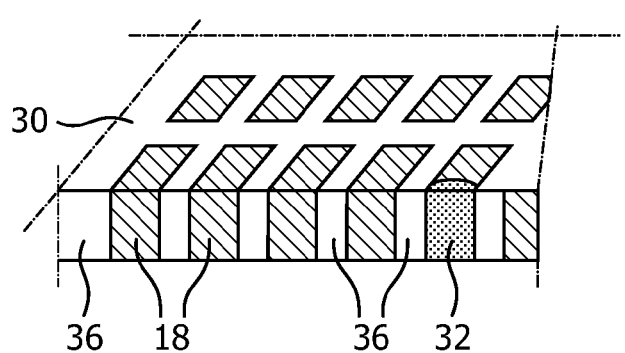
FIG. 2b illustrates a composite transducer array with a nonmagnetic via interconnect.

Construction of the composite piezoelectric transducer array begins with a sheet 30 of ceramic piezoelectric material as shown in FIGS. 2a and 2b. In a constructed transducer the sheet 30 is 1.2 mm thick (T). First, a number of holes are drilled through the sheet 30 where it is desired to have electrical connections from the back to the front (emitting side) of the transducer. The holes are then filled with silver-filled epoxy to form vias 32 through the sheet. The silver filling provides electrical conductivity and is non-magnetic for operation in a magnetic field of an MRI system. Other non-magnetic conductive material may be used for the conductive filling. The silver epoxy is cured. The sheet is then diced part-way through the thickness with parallel cuts 16 in one direction as shown in the view of the edge of the sheet 30 in FIG. 2a. Then the sheet is diced part-way through with parallel cuts in the orthogonal direction, leaving a plurality of upward projecting piezoelectric posts 18 and vias 32. The dicing cuts are then filled with non-conducting epoxy and partially cured. The top and bottom surfaces of the sheet are then machined flat to the depths indicated by dashed lines 34 in FIG. 2a. This will result in a finished sheet of a matrix of piezoelectric posts 18 and conductive vias 32 in epoxy 36 as shown in FIG. 2b. The finished sheet comprises a 1:3 matrix of piezoelectric posts, each of which has its dominant vibrational mode in its longitudinal direction through the thickness of the sheet, and which transmits ultrasound predominately in a direction toward the front (patient facing) side of the transducer. This predominant vibrational mode of the composite material reduces unwanted lateral transmission across the array to other active areas of the array.

Figure 4:
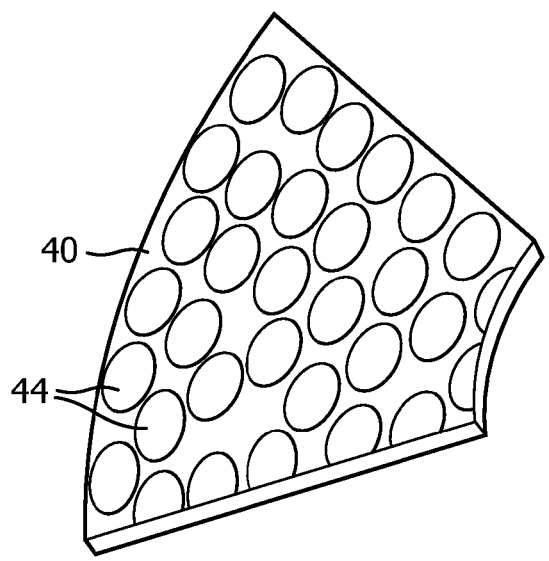
FIG. 4 illustrates a composite piezoelectric tile prior to spherical shaping for a HIFU transducer of the present invention.

The flat composite piezoelectric sheet 30 is machined to a trapezoidal shape as shown by the peripheral shape of the composite piezoelectric tile 40 of FIG. 4. In a constructed HIFU transducer the tiles have the trapezoidal shape of FIG. 4 to allow for a circular spherical center tile as described below. Alternatively, each tile may be machined in the shape of a slice of pie, so that the tiles will cover the matching layer without need for a center tile. The tiles could also take on other geometric shapes arranged to cover the spherical surface including but not limited to pentagons mixed with hexagons as demonstrated by the panels of a soccer ball. The flat trapezoidal tile of FIG. 4 is then given its desired spherical curvature. Since the composite transducer is formed of a matrix in epoxy, the tile can be heated to soften the epoxy so that the tile can be conformed to the desired curvature. This can be done by placing the tile 40 on a heated concave or convex fixture, then pressing the tile into conformance with the convex or concave shape. While the tile is held in the desired curvature, the fixture is cooled and the epoxy is allowed to fully cure. The result is a spherical-shaped composite piezoelectric tile for a spherical HIFU transducer.

Figure 3:
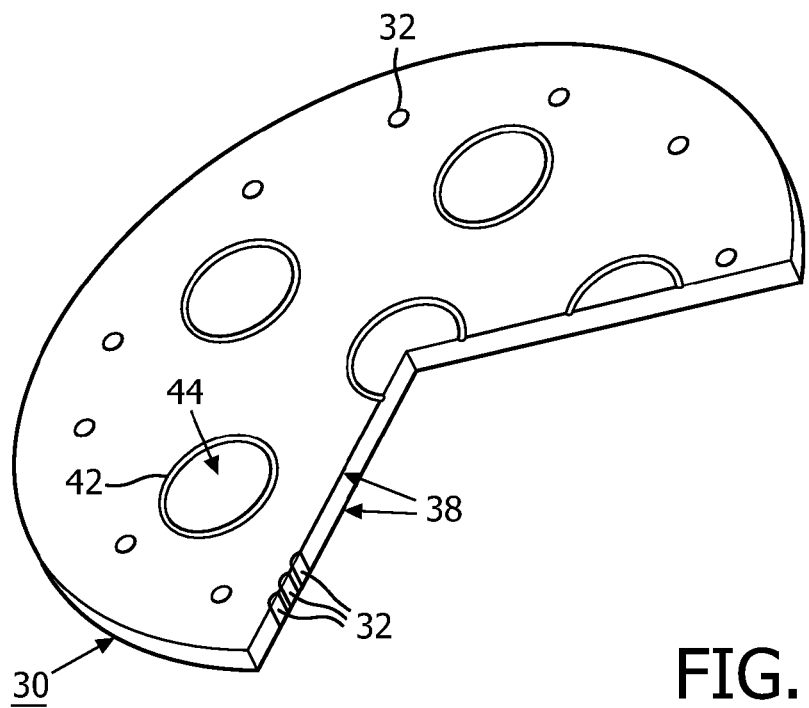
FIG. 3 illustrates a composite transducer array with emitting elements and nonmagnetic vias.

After the tile has been curved the top and bottom surfaces 38 are metallized by sputtering a conductive material onto the surfaces of the sheet as shown for the sheet 30 of FIG. 3. Preferably the conductive material is non-magnetic such as gold or titanium/gold. The metallized surfaces are electrically connected by the conductive vias 32, providing electrical connection from the back surface of the composite sheet to the front. Active (transmitting and receiving) areas of the composite piezoelectric sheet are then isolated by diamond core drilling, laser drilling, or ultrasonic machining around desired active areas from the back (convex) surface of the tile. Several such defined active areas 44 are shown in FIGS. 3 and 4. The cuts 42 which define the active areas cut through the metallization of the surface of the sheet to electrically isolate the areas and preferably extend over half-way through the composite sheet so as to acoustically isolate the active area from the surrounding areas of the sheet and other active areas. Alternatively, the active areas can be electrically and acoustically isolated after the tiles are bonded to the matching layer.

In a constructed tile the active areas 44 are not symmetrically arranged in rows or columns or circles or other regular patterns but are irregularly or randomly arranged as shown in FIG. 4. The random pattern prevents any significant additive combining of the acoustic sidelobes of the active areas which would diminish the effective energy delivered by the HIFU transducer.

Figure 5:
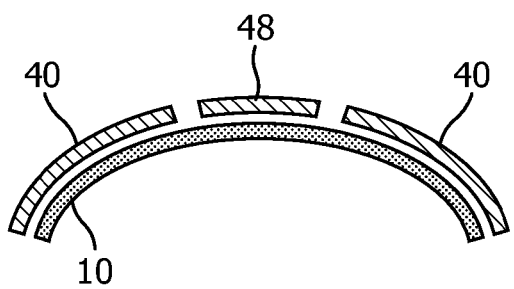
FIG. 5 illustrates in cross-section the placement of composite piezoelectric tiles on the matching layer for a HIFU transducer of the present invention.

Eight of the spherical trapezoidal tiles 40 are then thin bonded adjacent to each other around the convex surface 14 of the matching layer 10, which thereby provides a form for assembly of the tiles. If the spherical tiles 40 are pie-shaped as described above, the tiles will completely cover the convex side of the matching layer 10. When the spherical tiles are trapezoidal as shown in FIG. 4, they will cover the convex side of the matching layer except for the center of the matching layer. This circular spherical space can be left open. Alternatively it can be covered with a circular spherical thermal conductor such as aluminum for cooling. Returning acoustic energy will tend to be focused in the center of the HIFU transducer by virtue of its spherical geometric shape. Locating a thermal conductor here can aid in cooling the HIFU transducer. Alternatively, a circular spherical composite piezoelectric tile 48 can fill this space. For example, the circular sheet of FIG. 3, with its own active areas, can be formed into a spherical shape and located here, providing full composite piezoelectric coverage of the matching layer 10 as shown by the cross-sectional view of the trapezoidal and circular tiles on the matching layer 10 in FIG. 5. In a constructed transducer of this full coverage design, the nine tiles provide the HIFU transducer with 265 active areas, 256 for transmit and nine for receive.

It is seen in FIG. 3 that the vias 32 are located so as to connect the metallized area around the active areas on the back surface to the metallized surface on the front (patient-facing) side of the tile. In a constructed HIFU transducer the metallized area around the active areas 44 is electrically coupled to a reference potential. The vias 32 couple this reference potential to the metallized surface on the other side of the tile, the side not visible in FIG. 3. The vias are thus used to apply a reference potential to the patient-facing side of the composite piezoelectric tiles, and also to the metallization on the patient-facing side of the active areas 44. Since the patient-facing side of the tiles 40 are bonded to the matching layer 10 and are thus inaccessible for electrical connections, the vias provide the needed electrical connection through the piezoelectric sheet to the front side of the tile.

Figure 6:
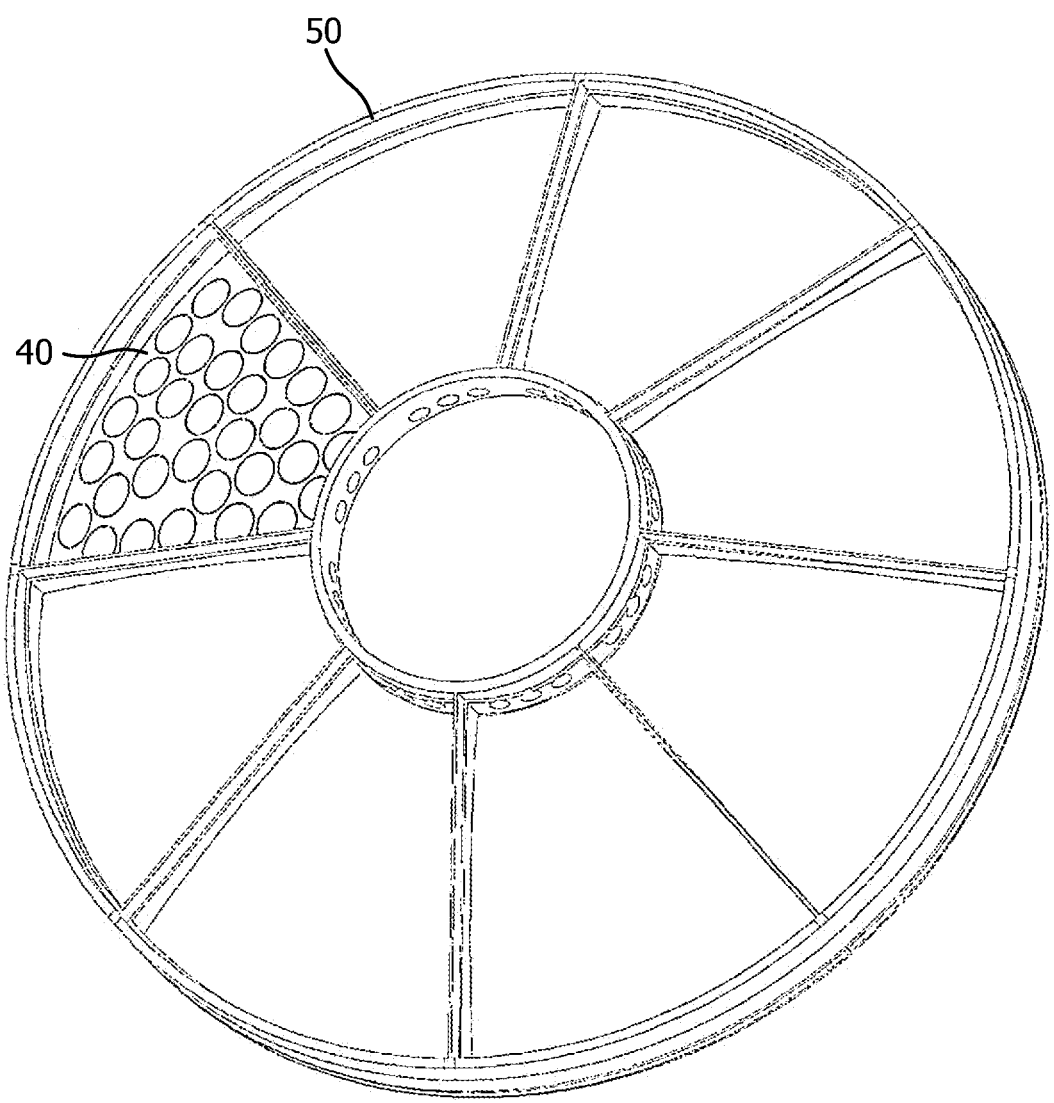
FIG. 6 illustrates in perspective the back of a nine-tile HIFU transducer of the present invention.
Figure 7A:
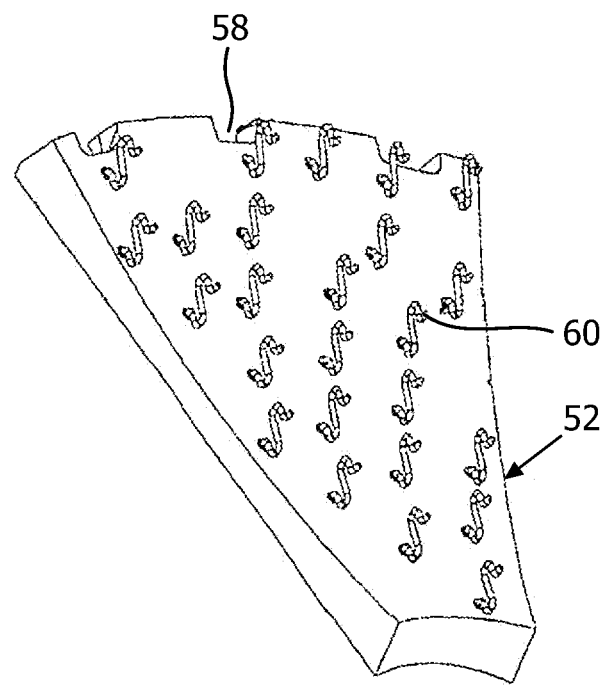
FIGS. 7a and 7b illustrate the front and back surfaces of a curved printed circuit board with extended compliant contacts for a HIFU transducer.
Figure 7B:
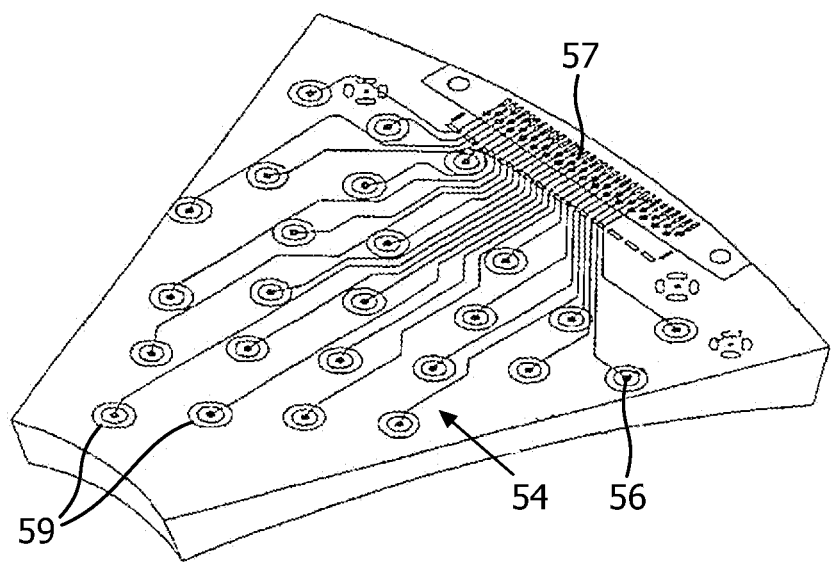

Next, a plastic support frame 50 is attached to the back of the assembled tiles by bonding, snap fit, or fasteners as shown in FIG. 6. In a constructed transducer each of the nine tiles 40,48 is accessible between the ribs of the support frame. The support frame is used to mount eight trapezoidal and one circular printed circuit boards 52 in a spaced relation above the back surfaces of the composite piezoelectric tiles 40. FIGS. 7a and 7b illustrate the front and back (54) surfaces of the trapezoidal printed circuit boards 52. Located on the back surface 54 are printed circuit connections 56 from a connector 57 which are connected by plated through-holes 59 through the board to active areas of the HIFU transducer. On the front surface of the printed circuit boards are compliant metallic contacts 60 which span the space between a printed circuit board and its tile and electrically connect the printed circuit connections to the active areas 44 and vias 32 of the opposing composite piezoelectric tile 40. Located at one edge of the printed circuit board 52 which is at the periphery of the HIFU transducer are cooling notches 58.

Figure 8:
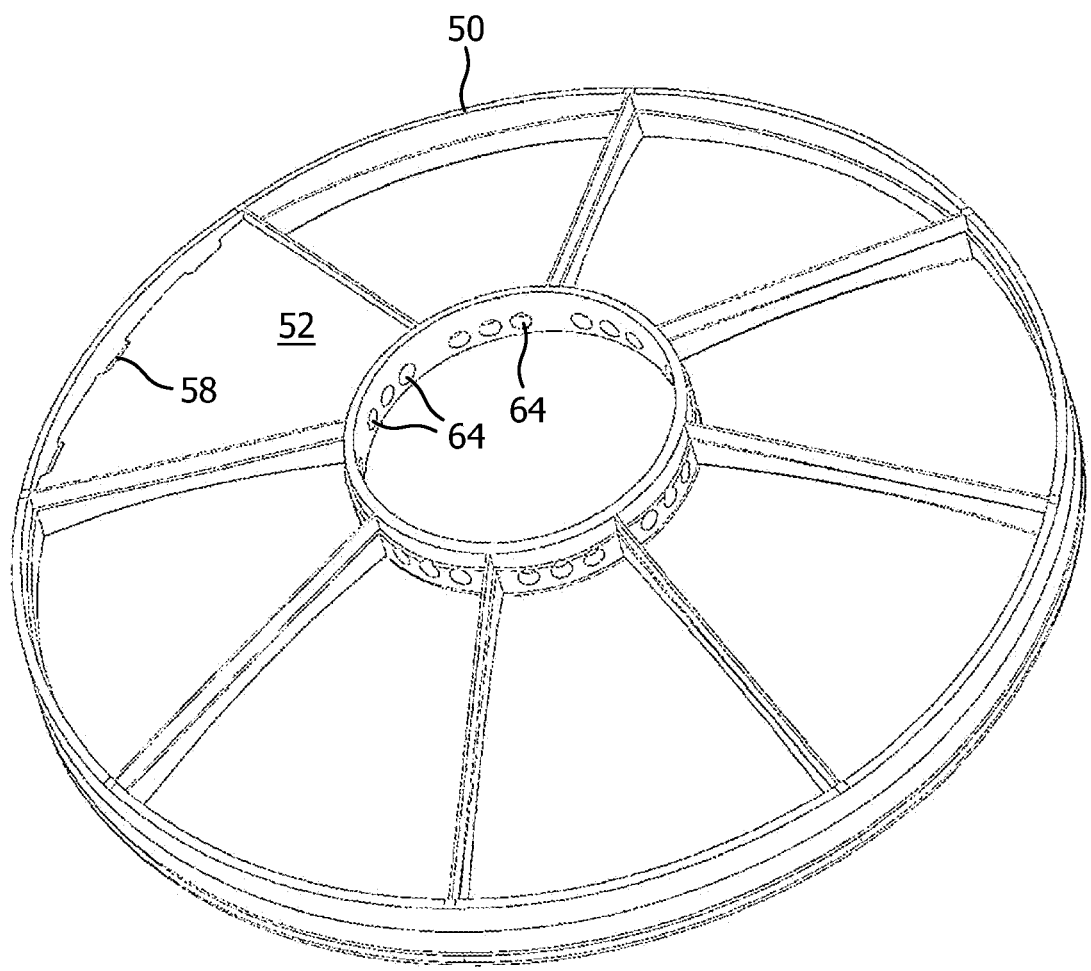
FIG. 8 illustrates in perspective the back of a HIFU transducer of the present invention with a support frame attached for the printed circuit boards of FIGS. 7a and 7b.

A printed circuit board 52 is bonded to the support frame 50 above each tile such as tile 40 shown in FIG. 6. When a printed circuit board is assembled in this manner it appears as shown by printed circuit board 52 in FIG. 8. Before this assembly, the extended ends of the compliant metallic contacts 60 are coated with conductive epoxy. When the printed circuit board is assembled on the frame, the ends of the contacts 60 will contact metallized areas of the opposing tile and become bonded in electrical connection with the metallized areas when the conductive epoxy cures. The contacts 60 thus provide electrical communication between the printed circuit boards and active and reference potential areas of the piezoelectric tiles.

While the printed circuit boards can be fabricated as conventional planar printed circuit boards, the printed circuit board 52 of FIGS. 7a and 7b preferably have a spherical curvature, matching that of the opposing composite piezoelectric tiles 40 to which they are connected by the contacts 60. The printed circuit boards can be curved on just the side facing the tile as shown in FIG. 7a, or on both sides. The printed circuit boards can be formed as curved boards in several ways. One is to start with a thick planar sheet of glass epoxy board material and machine or grind the surface of the board to the desired curvature. The other technique is to use thermoforming to heat the board material and soften the epoxy, then form the curvature by compressing the sheet against a fixture of the desired curvature. The circuit boards can be double-clad with photo-imaged and chemically-etched conductive lines on the top and bottom surfaces interconnected by plated through-holes formed in the boards. The circuit boards can also be multilayer boards with three or more layers of conductive lines formed on the surfaces and within layers of the board for more complex, higher density circuit configurations. The rigid boards 52 are also capable of securely mounting other electrical components such as the connector 57.

In accordance with the principles of the present invention, a modular removable cavitation sensor is located at the center of the HIFU transducer as illustrated by the rear view of the transducer shown in FIG. 9. In this view the printed circuit boards 52 are removed and the rear of the tiles 40 in the frame 50 are visible. A circular printed circuit board in the center of the frame 50 for making connections to the cavitation sensor is also removed so that the modular assembly for the cavitation sensor is visible. The cross-hatched area in the center of the HIFU transducer is the location of a cavitation sensor 90. An enlarged view of the center of the HIFU transducer is shown in FIG. 10.

In the enlarged view of FIG. 10, an opening is located in the center of the HIFU transducer which is encircled by a rearward extending cylindrical printed circuit board mount 94. The mount 94 projects to the rear from the annulus of the center opening and is threaded in its inner cylindrical surface. A threaded modular housing 92 is located inside the threaded printed circuit board mount forward from the location of the printed circuit board. The engagement of the two threaded surfaces is indicated at 106. The cavitation sensor 90, a piezoelectric receive element, is located in the housing 92. The piezoelectric receive element may be formed from solid piezoelectric ceramic, a composite ceramic formed by dicing a piezoelectric ceramic disk at right angles and filling the dicing cuts with epoxy filler, or an element made of piezoelectric PVDF material. In either case, the piezoelectric element is ground or lapped to a thickness which achieves the desired receive frequency. The outer surfaces of the piezoelectric element are metalized to provide signal and return contacts. A circular isolation cut 104 is formed in the rear surface of the piezoelectric element to separate the metallization on the rear surface into two contact electrodes, a circular contact electrode 98 in the center of the rear surface and an annular peripheral contact electrode 96 which is contiguous with the metallization on the front of the element. The element is then electrically poled. A matching layer 100 is bonded to the front surface of the piezoelectric element 90.

FIGS. 11 and 12 are cross-sectional views of the modularly housed cavitation sensor installed in the HIFU transducer 120, with FIG. 12 showing the central assembly in an enlarged view. The modular cavitation sensor housing 92 is seen with its centrally bonded piezoelectric sensor element 90 which is faced with the matching layer 100. An O ring 102 is placed around the modular housing 92 before the threaded exterior of the housing is screwed into the matching threads of the printed circuit board mount 94. When the modular housing 92 is fully screwed in place, the O ring 102 is compressed between the modular housing 92 and the mount 94 to form a liquid tight seal around the housing. When the housing 92 is seated in this manner, electrical contacts 112, 114 extending from printed circuit board 110 make electrical contact with the metalized contact electrodes 98, 96 of the piezoelectric element. These contacts couple piezoelectric signals received by the element 90 to circuitry on the printed circuit board 110, from which the received signals, which may be indicative of cavitation, are coupled to electrical circuitry and processed.

Should the cavitation sensor become damaged during manufacturing or during use, the damaged cavitation sensor can be replaced by unscrewing the modular housing 92 and sensor element 90 from the transducer 120. In a constructed embodiment multiple holes are formed in the patient-facing side of the modular housing 98 for engagement of a spanner wrench to thread and unthread the housing from the transducer mount 94. After the damaged sensor element is unthreaded and removed, a new modular housing and sensor element are threaded back into the opening until the O ring 102 is compressed again to form the fluid seal. The resilient spring contacts 112, 114 of the printed circuit board 110 make contact with the electrodes 98, 96 on the new sensor and the HIFU transducer with its new sensor is then ready to be put back into service.

What is claimed is:

1. A high intensity focused ultrasound (HIFU) transducer having a replaceable cavitation sensor comprising:
   a dish-shaped HIFU transmitter having a central region, wherein the HIFU transmitter comprises a plurality of separated composite piezoelectric tiles mounted to a support frame, wherein the separated composite piezoelectric tiles are accessible between ribs of the support frame;
   a plurality of separated printed circuit boards (PCBs) mounted to the support frame above respective ones of the plurality of separated composite piezoelectric tiles, wherein the support frame maintains a spaced relation between the plurality of separated PCBs and respective ones of the plurality of separated composite piezoelectric tiles;
   a cavitation sensor; and
   a modular housing which contains the cavitation sensor, the modular housing being removably located in the HIFU transmitter so that the cavitation sensor is positioned to receive acoustic signals which may be indicative of cavitation.

2. The HIFU transducer of claim 1, wherein the dish-shaped HIFU transmitter has a spherical patient-facing surface.

3. The HIFU transducer of claim 1, wherein the cavitation sensor further comprises a piezoelectric transducer.

4. The HIFU transducer of claim 3, wherein the piezoelectric transducer further comprises a piezoelectric element formed as one of a) solid piezoelectric ceramic; b) a composite ceramic formed by dicing a piezoelectric ceramic disk and filling the dicing cuts with filler material; or c) an element made of piezoelectric PVDF material.

5. The HIFU transducer of claim 4, wherein the piezoelectric transducer has exterior surfaces which are metalized to provide first and second electrodes.

6. The HIFU transducer of claim 5, wherein the piezoelectric transducer further comprises an isolation cut which electrically separates a metalized exterior surface into separate electrodes.

7. The HIFU transducer of claim 1, wherein the modular housing is removably located in the central region of the HIFU transmitter.

8. The HIFU transducer of claim 7, wherein the central region further comprises a threaded opening; and wherein the modular housing is threaded to removably engage the threaded opening of the central region.

9. The HIFU transducer of claim 8, further comprising a printed circuit board located in the central region, the printed circuit board having electrical contacts; wherein the cavitation sensor further comprises electrodes which are engaged by the printed circuit board electrical contacts when the modular housing is threaded into the central region.

10. The HIFU transducer of claim 8, wherein the modular housing is further formed to be engaged by a tool to thread the modular housing into the central region.

11. The HIFU transducer of claim 10, wherein the modular housing is further formed with multiple holes suitable for engagement by a spanner wrench.

12. The HIFU transducer of claim 8, further comprising a liquid-tight seal which is engaged between the modular housing and the HIFU transmitter when the modular housing is fully engaged in the HIFU transmitter.

13. The HIFU transducer of claim 12, wherein the liquid-tight seal further comprises an O ring seal.

14. The HIFU transducer of claim 9, wherein the printed circuit board electrical contacts further comprise resilient contacts.

15. The HIFU transducer of claim 14, wherein the resilient contacts further comprise spring contacts.

16. The HIFU transducer of claim 1, wherein the plurality of separated PCBs comprise compliant metallic contacts which span the spaced relation between the plurality of separated PCBs and respective ones of the plurality of separated composite piezoelectric tiles, wherein the compliant metallic contacts are coated with conductive epoxy.

17. The HIFU transducer of claim 1, wherein each of the plurality of separated PCBs include cooling notches on an edge.

18. The HIFU transducer of claim 6, wherein the first electrode is a circular contact electrode and the second electrode is an annular peripheral contact electrode.

19. The HIFU transducer of claim 8, wherein the threaded opening of the central region is a threaded opening of the support frame.

20. The HIFU transducer of claim 19, wherein the threaded opening of the support frame comprises a rearward extending cylindrical printed circuit board mount.

* * * * *